United States Patent [19]

Datta

[11] Patent Number: 4,885,247

[45] Date of Patent: Dec. 5, 1989

[54] RECOVERY AND PURIFICATION OF LACTATE SALTS FROM WHOLE FERMENTATION BROTH BY ELECTRODIALYSIS

[75] Inventor: Rathin Datta, Chicago, Ill.

[73] Assignee: Michigan Biotechnology Institute, East Lansing, Mich.

[21] Appl. No.: 183,061

[22] Filed: Apr. 19, 1988

[51] Int. Cl.⁴ ................................................. C12P 7/56
[52] U.S. Cl. ..................................... 435/139; 435/261; 204/182.4; 204/182.6
[58] Field of Search ........................... 435/41, 261, 139; 204/182.4, 182.6

[56] References Cited

U.S. PATENT DOCUMENTS

| | | | |
|---|---|---|---|
| 4,110,175 | 8/1978 | Ahlgren et al. | 204/180 P |
| 4,678,553 | 7/1987 | Mundle et al. | 204/182.6 |
| 4,698,303 | 10/1987 | Bailey et al. | 435/139 |
| 4,711,722 | 12/1987 | Toyoski et al. | 210/638 |

FOREIGN PATENT DOCUMENTS 2555200  5/1985  France.

OTHER PUBLICATIONS

Hongo, M., Nomura, Y. and M. Iwahara, "Novel Method of Lactic Acid Production by Electrodialysis Fermentation", *Appl. Environ. Microbiol.* 52, 2, 314–319, Aug. 1986.

Nomura, Y., Iwahara, M. and M. Hongo, "Lactic Acid Production by Electrodialysis Fermentation Using Immobilized Growing Cells", *Biotechnol. & Bioeng.* 30, 788–793, Oct., 1987.

"AQUATECH" System, Product Brochure, Allied Signal Corporation, 1985.

Primary Examiner—Barry S. Richman
Assistant Examiner—Lyle Alfandary-Alexander
Attorney, Agent, or Firm—Quarles & Brady

[57] ABSTRACT

A process for producing, recovering and purifying lactate from a fermentation broth so that it can be efficiently and economically converted to lactic acid is disclosed. The process comprises growing a high lactate producing, microorganism on an inexpensive substrate until a whole broth containing about 75 to about 90 grams of lactate salt is obtained. The whole broth including the viable cells is then electrodialyzed in a unit having anionic-permeable and cationic-permeable membranes to cause the lactate salt to concentrate in an aqueous liquid which can be treated to convert the lactate salt to lactic acid.

10 Claims, 1 Drawing Sheet

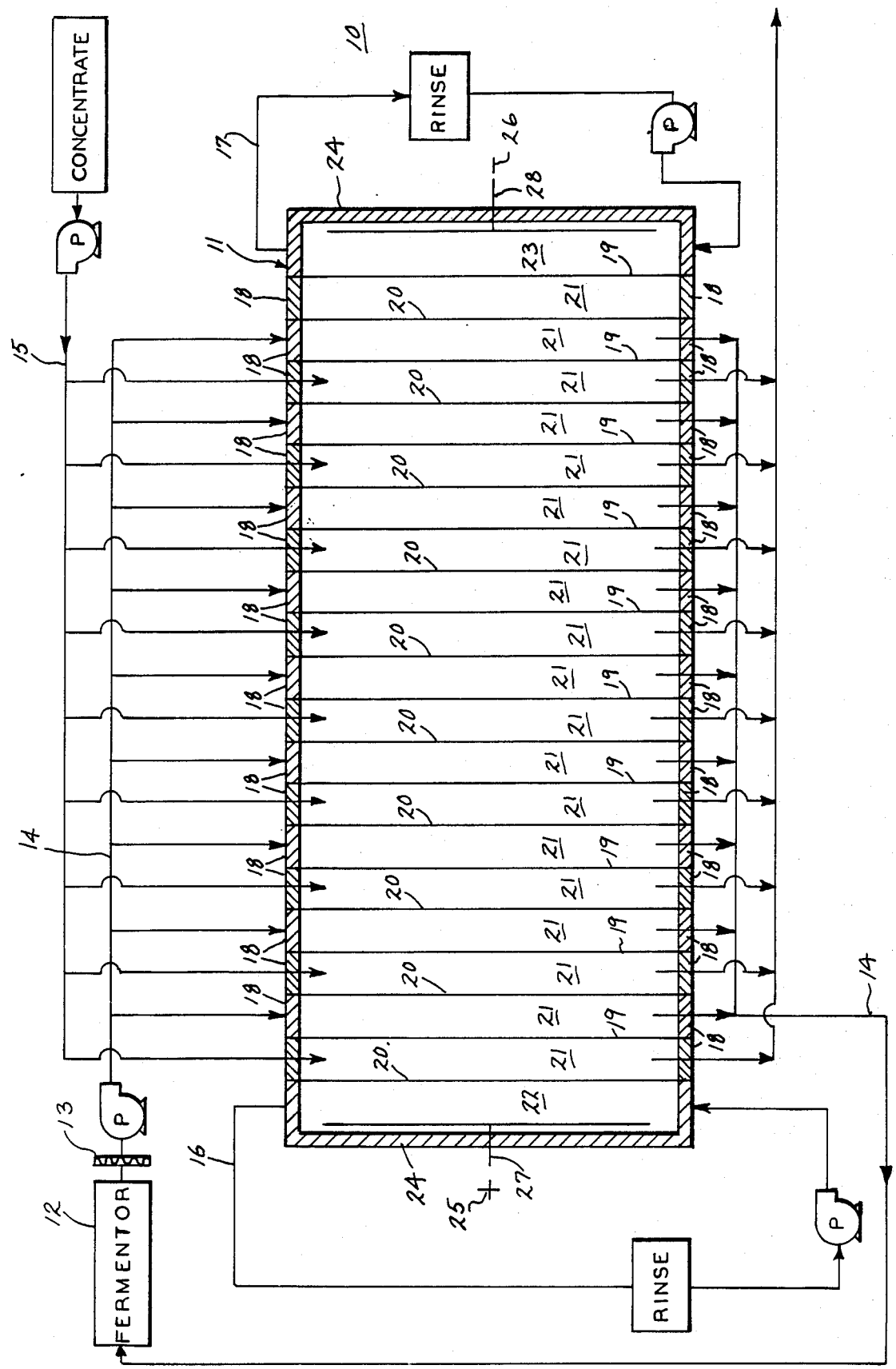

RECOVERY AND PURIFICATION OF LACTATE SALTS FROM WHOLE FERMENTATION BROTH BY ELECTRODIALYSIS

FIELD OF THE INVENTION

The present invention relates to the recovery and purification of organic acid salts from fermentation broths More particularly, it relates to the recovery and purification of lactate salts from fermentation broths by electrodialysis.

BACKGROUND OF THE INVENTION

Lactic acid is a specialty chemical used in the food and chemical industries. It is a potential commodity chemical because it can be used to make polymers or hydrogenated to make propylene glycol and other three carbon chemical intermediates. Currently, lactic acid is expensive to make by fermentation because the fermentation produces a crude lactate salt from which the cells and protein have to be removed. To be an economical source of lactic acid, the fermentation has to employ a microorganism which produces high concentrations of lactate from inexpensive substrates. In addition, the recovery, separation and recycle of viable cells and nutrients to the fermentor is required because high cell density and fermentation productivity and low nutrient consumption are important.

Electrodialysis (ED) is a well known separation process where ionized compounds are separated from non-ionized or weakly ionized compounds in aqueous solutions based on transport through ion exchange membranes in an electric field. The process has been used in a commercial scale in the chlor-alkali, desalination, metal-processing, waste-water treatment, pharmaceutical and food processing industries. Since in a fermentation broth the lactate salt is ionized, whereas the carbohydrates and proteins and amino acids are either non-ionized or weakly ionized, recovery and purification of lactate salts from a fermentation broth by electrodialysis is feasible Recently several papers have been published on the recovery and the purification of lactate from fermentation broths. In the published processes, the broth was either thoroughly cleaned to remove cells and proteins prior to electrodialysis or when the whole broth, containing cells, was used the membrane fouled and led to a loss of efficiency.

Prigent (1) disclosed a method for production of lactate from fermenting whey where the broth was filtered by ultrafiltration to remove the cells and then electrodialyzed. Hongo, Nomura and Iwahara (2) used a whole broth of *Lactobacillus delbrueckii* IFO 3534 in their electrodialysis apparatus, but discovered that the efficiency was poor due to membrane fouling. These workers (3) then devised a complicated fermentation process where the cells were immobilized in alginate beads and the cell-free broth was fed to the electrodialyzer. The described processes are not practical for commercial use because bacterial cells are very small and removing the cells by high speed centrifugation and/or ultrafiltration is expensive. Cell immobilization in alginate beads also is very expensive and not readily adaptable to commercial use.

For a fermentation process to be economically attractive to produce lactic acid as a commodity chemical, it must be simple and inexpensive. Ideally, the microorganism should grow on low cost substrates and nutrients; the rate of fermentation should be high (high productivity); the lactate concentration in the fermentation broth should be high; and, an inexpensive recovery and purification process should be available.

SUMMARY OF THE INVENTION

It is a general object of the present invention to disclose a new and improved process for the production of organic acid salts and their recovery and purification from whole fermentation broths.

It is a further object to disclose an inexpensive fermentation process for producing lactate salts on a low cost medium using a novel strain of *Lactobacillus acidophilus*.

It is a further object to disclose an electrodialysis process for the recovery and purification of lactate salts from whole fermentation broth without having to first remove the microbial cells.

It is another object to disclose an improved process for producing lactate salts by fermentation which includes recycling the microbial cells back to the fermentor where they can produce additional lactate.

The manner in which these and still other objects are accomplished will become apparent to those skilled in the art from the following description and accompanying drawings.

The present invention basically comprises growing a microorganism capable of producing at a cell concentration of $2.5 \times 10^{10}$ to $3.0 \times 10^{10}$ cells/ml least about 2 grams of lactate per liter of broth per hour on an inexpensive substrate at a pH of about 5.0 to about 5.7 and a temperature of about 35° to about 45° C. until the broth contains about 75 to about 90 grams of lactate per liter of broth. The whole broth is then strained to remove larger then cell particles and electrodialyzed in a unit containing anionic permeable membranes and cationic permeable membranes under conditions which cause the lactate ions to leave the broth and to concentrate in an aqueous liquid from which the lactate can be removed and converted to lactic acid using known techniques and equipment. The viable microbial cells from the whole broth are recycled to the fermentor where they economically produce additional lactate.

The preferred microorganism is a strain of *Lactobacillus acidophilus* IAM 3532; it produces high yields of lactate at cell concentrations of about $2.5 \times 10^{10}$ to about $3.0 \times 10^{10}$ cells per ml. The preferred membranes are the anionic exchange and cationic exchange membranes available from Asahi Glass Co. under the names SELEMION AMV and CMR, respectively.

BRIEF DESCRIPTION OF THE DRAWING

The drawing is a schematic diagram of an electrodialysis apparatus in which the preferred embodiment of the method of the present invention may be carried out.

DESCRIPTION OF THE PREFERRED EMBODIMENT

The drawing schematically illustrates the electrodialysis apparatus 10 which includes a cell stack 11, a fermentor 12, a screen 13, a feed solution injection, recirculation and removal system 14, a concentrate recirculation and removal system 15, an anolyte rinse system 16 and a catholyte rinse system 17.

It will be appreciated the apparatus illustrated in the drawing is for purposes of illustration and modifications thereof can be made by those skilled in the art without departing from the scope of the present invention.

Cell stack 11 may be any known type of membrane assembly such as a plate and frame assembly wherein a plurality of suitably perforated flow distribution gaskets 18 support and seal the peripheries of a plurality of cation-permeable membranes 19 and anion-permeable membrane 20 in parallel spaced relation to form a series of parallel cells 21 and end cells 22 and 23. Each cell 21 is defined by a pair of membranes 19 and 20 and a gasket 18. The end cells 22 and 23 are respectively defined by a membrane 19 and a membrane 20 and end caps 24. Disposed within end cell 22 is a suitable anode 25 and a cathode 26 is disposed in the opposite end cell 23. Anode 25 and cathode 26 are connected respectively to the positive and negative terminals of a suitable power source (not shown) through leads 27 and 28. Cell stack 11 also includes suitable couplings (not shown) for admitting and removing liquids from each of cells 21. The components of the cell stack 11 can be held in an abutting relation by suitable clamps or tie rods (not shown).

The membranes 19 are anion-permeable and cation-impermeable and the membranes 20 are cation-permeable and anion-impermeable membranes. Suitable materials for use as membranes 19 and 20 include anion and cation exchange resins having active ion capture sites, respectively. The preferred membranes 19 are fabric reinforced microheterogeneous interpolymer membranes, such as the anion exchange membranes manufactured by Asahi Glass Co. SELEMION AMV membranes, while the preferred membranes 20 are the SELEMION type CMR cation exchange membranes available from the same source. The membranes are described in U.S. Pat. No. 4,678,553 and others. Properties for these two membranes are set forth in Table I.

In the preferred practice of the invention, the whole broth is pumped from the fermentor 12 through the screen 13 which removes larger than cell size particles. The whole broth, minus those particles, is transported via system 14 to the cells 21 where it is subjected to an electrical current which causes the lactate ions to migrate through the anionic-permeable membrane 19 into an 1.0M ammonium lactate solution which is circulating in the system 15 on the other side of the membrane 19. The lactate enriched ammonium lactate solution, also called the concentrate, is transmitted to a second water splitting electrodialysis apparatus (not shown) to convert the lactate to lactic acid. The feed solution, minus the lactate, but including the viable cells is recirculated via the system 14 to the fermentor. While the electrodialysis is going on the electrodes are rinsed with a suitable electrolyte solution such as 0.1 to 0.4M $Na_2SO_4$ in water circulated by the rinse systems 16 and 17. The process can be operated on either a batch or continuous basis.

TABLE 1

TYPES AND PROPERTIES OF SELEMION MEMBRANES

| DESIGNATION Type | | CMR Strongly acidic cation-permeable membrane ($Na^+$ type) | AMV Strongly basic anion-permeable membrane ($Cl^-$ type) | REMARKS |
|---|---|---|---|---|
| Transport number | T $Na^+$ | Over 0.92 | — | Calculated from the membrane potentional: |
| | T $Cl^-$ | — | Over 0.94 | 0.5/1.0 mol/P NaCl solution at 25° C. |
| | T$Ca^{++}$ + $Mg^{++}$ | Under 0.04* | | Measured by electrodialysis of sea water at 2A/$dm^2$ |
| Resistance per unit area | X-$cm^2$ | 2.0–2.3 | 2.0–3.0 | Measured by 1000 Hz-AC 0.5 mol/P NaCl at 25° C. |
| Thickness | mm | 0.13–0.15 | 0.12–0.15 | |
| Bursting stength kg/$cm^2$ | | 3–4 | 3–5 | |
| Use | | General desalination/ concentration Sea water concentration | General desalination/ concentration | |

*After treatment

The practice of the invention is further illustrated by the following example.

EXAMPLE

MATERIALS AND METHODS

Electrodialysis Unit

The electrodialysis apparatus consisted of a stack of the type shown in the drawing which comprised an alternating series of anion and cation selective membranes separated by flow distribution gaskets. The membranes were bound on one end by an anolyte compartment and an anode on the other end by a catholyte compartment and cathode. The stack pack for evaluation was provided by HPD Inc. (Naperville, IL) and contained membranes manufactured by Asahi Glass Co. (Japan). The stack pack contained the following: 9 cell pairs anion membrane—AMV
cation membrane—CMR
effective area—178 $cm^2$
electrolyte—0.1 to 0.4M $Na_2SO_4$ The unit consisted of three independent flowchannels fed to the electrodialyzer stack pack. The three streams were:

(1) the feed stream—whole broth from the fermentor
(2) concentrate stream—initially a 1.0M ammonium lactate solution which is further enriched by lactate from the feed product
(3) electrolyte—0.1 to 0.4M sodium sulfate From each reservoir, material was pumped through a valve, rotameter, and pressure gauge, to the stack pack, and then back to the reservoir. Another set of five gallon containers was located below each reservoir for removal purposes. The whole unistrut frame was on wheels so it could be easily moved.

The electrical current was supplied by a Hewlett Packard (HP) regulated DC power supply model 62688. It was connected to the anode and cathode of the membrane stack which could produce 0–20 amperes and deliver 0–50 volts. Another voltmeter was used to measure the voltage drop across the membranes (excluding electrodes). Two platinum wires were inserted between eight cell pairs of membranes and then connected to the voltmeter.

Fermentation Broth

The feed material, ammonium lactate fermentation broth of *L. acidophilus* IAM 3532, was produced using a fermentor in the pilot plant.

The anaerobic fermentation was performed at 39° C. in the fermentor with a working volume of 150 L for 69 hours. The media contained approximately 10% dextrose (Cerelose), 2% corn steep liquor, and 0.2% corn oil. A 4% inoculum was used. The pH was maintained between 5.3–5.5 by addition of ammonium hydroxide on a demand basis. Agitation speed was maintained at 100 rpm.

For one set of experiments the cells in the fermentation broth were removed by processing the broth through a high speed Westphalia centrifuge. The broth was then filtered with supercel precoat in a vacuum filter.

For the second set of experiments freshly prepared whole broth using the same media and similar fermentation conditions (pH=5.3–5.5, temp. 35°–40° C.) was used for the whole broth experiments. The broth was screened through a 200 mesh wire screen to remove larger than cell size particles before electrodialysis.

Permissible Current Density (PCD) Determination

Before making actual runs, permissible current density (PCD) was determined to obtain a safe range for operating current density. For these runs, only two reservoirs were used. One reservoir supplied broth to both the diluting and concentrating compartments and then was pumped back to the reservoir. The second reservoir was for the electrolyte.

The unit was operated at low current and the voltage was recorded every 30 seconds for a period of 30 minutes to two hours. If the voltage remained constant over time, the procedure was repeated at a higher current. This procedure was continued until a point was reached when the voltage began to increase with time denoting the onset of polarization or fouling. The current density at that point was the PCD for that operating condition (salt concentration, pH, temperature, and linear velocity).

Runs were made at 4, 5, 6, 7, 10 and 12.5 amps each for 30 minutes using broth containing 1M ammonium lactate at 50° C. and 5 cm/sec linear velocity. The initial operating current and current density (12 amp, 67 mamp/cm$^2$) was decided upon based on the PCD results.

Batch Electrodialysis Description

The system was operated in a batch mode. Thus, the lactate broth was continually being demineralized. The electrodialysis process continued until the solution was demineralized to a desired degree. The following is a description of the operating procedure.

Charging

1. Drain the system (Note: the system should be filled with demineralized water at all times to keep membranes from drying out) and close the valves.
2. Fill the diluting reservoir with the solution to be demineralized, 6–14 liters of ammonium lactate broth.
3. Fill the concentrating reservoir with one liter of ammonium lactate of a concentration similar to that of the diluting compartment. This ensures good initial conductivity and circulation rate in the concentrating compartment. (Ammonium lactate was prepared from Fisher Lactic Acid and pH adjusted to 5.2 with ammonium hydroxide).
4. Fill the electrolyte reservoir with 4–6 liters of 0.1 to 0.4M $Na_2SO_4$ or other suitable electrolyte.
5. Open valves and turn on pumps. Allow liquid in all three lines to flow at a rate that the floats in the rotameter are barely lifted.
6. Open valves allowing pressure in the lines to build up gradually such that the pressure differential between any two lines at no time exceeds 1 psig.
7. Continue opening valves until the desired flowrate is reached.
8. Turn on steam line to heat the diluting stream to desired temperature.

Membrane Equilibration

1. Turn on power supply to a reading of 0.2 amperes.
2. Continue running the system for 10 minutes.

Batch Operation

1. Set valves to desired flow rates.
2. Set power supply for desired current (the desired current was previously determined based on the permissible current density).
3. During the run, data collected included: current, voltage drop across total unit, voltage drop across eight cell pairs, volume levels in the diluting and concentrating compartments, pH of the diluting and electrolyte compartments, conductivity of the diluting compartment, and temperature of the diluting compartment.
4. The unit was operated at a constant current until the resistance started to increase thus increasing the voltage drop across the unit. At that time, a maximum voltage was set and the current was allowed to decrease until the end of the run.
5. Samples were taken at thirty minute intervals in addition to initial and final samples.

Analytical Methods

Conductivity was measured using a portable conductivity meter (Cole Parmer model 1484-10).

Lactate concentration reported is the anion concentration and was measured after appropriate dilution and acidification by an HPLC method using a 1 ft. long HPX87 H+ column of BioRad (Calif. U.S.A.).

Amino Acids—a semiquantitative assay method to measure L-amino acids in presence of ammonium salts was developed based on two coupled enzymatic reactions, L-amino acid oxidase and peroxidase. This method allowed rapid determination of L-amino acids using L-leucine as a standard. Total and free amino acids for important samples were determined by Hazelton Laboratories (Wis. U.S.A.) using standard methods of ion exchange chromatography.

Definition of Terms

Current Density—current per unit area of available membrane through which current passes. The higher the applied current density, the lower cell area required to achieve a specific degree of ion transfer.

Current Efficiency—ratio of the number of equivalents of lactate transferred to the number of Faradays of electricity passed through the membrane.

Flux—volume transferred through the membrane in a specific time and available area.

Data and calculation details from an electrodialysis run are presented in Tables 2–4.

RESULTS

Electrodialysis of Centrifuged and Filtered Broth

Batch electrodialysis of centrifuged and filtered broth which contained no cells was run in the ED stack pack. Table 2 shows the results of two different runs. As can be seen from the data, this particular strain of *L. acidophilus* produces a high lactate anion concentration (75–85 g/l) in the broth using a simple media consisting of a carbohydrate, corn steep liquor and small quantities of crude corn oil. The overall productivity in the batch fermentation was between 2–2.5 g/l hr. Electrodialysis of this broth performed very efficiently with current efficiencies of 90 ($\pm$2)% and at high current densities. High lactate concentration in the concentrate product also was achieved due to good flux and low water transfer rate through the membranes. The concentrate product was also highly purified and >90% of the amino acids was retained in the broth while 92% of the lactate was removed from it.

Electrodialysis of Whole Fermentation Broth

The next set of experiments was made with whole culture lactate broth without cell removal (containing 2.5–3×$10^{10}$ cell/ml). The first was a batch run to determine feasibility which was followed by a second batch run at a slightly lower temperature, 45° C., to maintain viability of the cells. In the second run, the electrodialyzed broth was returned for further fermentation. No irreversible fouling was detected during the course of either run. The results of these runs are shown in Table 3.

Comparing the whole broth to filtered broth runs, slightly less lactate was removed but the current efficiency remained high (90–91%). Water transfer rates were similar so there was still a 2.5× concentration of product lactate across the membrane. The slightly higher electricity requirement for the last run is due to the lower operating temperature (45° vs. 50° C.). Temperature is directly related to conductance (inverse of resistance) and energy requirement is directly related to resistance. This would be a small penalty to pay to maintain cell viability.

During the whole broth electrodialysis run, samples of the whole broth were assayed for viable cells (by plate count on MRS agar media). The cells remained predominantly viable.

Whole Broth Recycle Fermentation

The spent broth from the electrodialysis apparatus was further recycled to the fermentor and fermented with additional dextrose, corn oil (0.2%), and different concentrations of corn steep liquor (F2-1.4%, F3-2.4%, F4-0%). The fermentation volume was made up to the original broth volume (0.7 liter to 1 liter). The viable cell count for F2 and F3 at the beginning of recycle fermentation was comparable to the cell count in the electrodialyzer feed broth. The recycle fermentations F2 and F3 proceeded rapidly producing 77 and 85 g/l lactate respectively in 24 hours with productivities of 2.2 and 2.5 g/l-hr, respectively. These are comparable to that obtained in typical batch fermentations, 2–2.5 g/l-hr. Recycle fermentation F4 (0% CSL) was slow and required 100 hours to consume the dextrose and produce 90.4 g/l lactate. This result shows that viable cells from the electrodialysis of whole broth can be recycled and used to ferment more carbohydrates to lactate without losing productivity and the ability to produce high lactate concentration.

Protein and Amino Acid Transport

An analytical method was developed using the enzymes L-amino acid oxidase and peroxidase in a semi-quantitative method for quick analyses of free L-amino acids. This assay is very useful in determining the gross performance of membranes during an electrodialysis run. The amino acid rejection data in TABLES 2 and 3 are based on this assay and clearly show a very high retention of amino acids in the broth and purification of lactate in the product concentrate.

To obtain a more detailed understanding of the protein and amino acid transport, samples from key ED runs were analyzed for complete amino acid analysis. The data is summarized in Table 4. The data shows that the product concentrate contains only a small fraction (10–15%) of the total and free amino acids from the feed broth, which means that 85–90% of the proteins and amino acids are rejected. It also shows that electrodialysis of whole broth performs very well for protein and amino acid rejection and a highly purified concentrate can be obtained by a one step process by electrodialysis of whole broth.

It will be apparent to those skilled in the art that the process of the present invention is a low cost fermentation process which can produce lactic acid and its derivatives as specialty and commodity chemicals, using low cost nutrients. The process also produces a high lactate product concentration at a high productivity and an economical purification process.

The preferred strain of *Lactobacillus acidophilus* IAM 3532 grows well on media containing carbohydrates, corn steep liquor and low concentration (0.2%) of crude corn oil. In addition, it produces high concentrations of lactate (75–90 g/l) with a high productivity 2–2.5 g/l hr.

During the electrodialysis of whole broth with viable cells no irreversible membrane fouling was observed. Hence, the factors that determine the economic and process feasibility of electrodialysis--high current efficiency, low energy consumption, high selectivity and purification, high flux, high current density could be achieved using whole broth. Other practitioners (1,2,3) have performed electrodialysis of lactate fermentation broth either after extensive and costly ultrafiltration, microporous filtration or centrifugation to remove and recycle cells; or have found irreversible membrane fouling leading to loss of efficiency; or used expensive and complex cell immobilization methods to retain cells in the fermentor and avoid introduction of cells into the electrodialyzer.

The combination of the special strain of *Lactobacillus acidophilus* IAM 3532 and the use of fabric reinforced, microheterogeneous interpolymer membranes (Asahi Glass AMV and CMR) permits simultaneous electrodialysis and cell recycle from whole broth to be achieved without loss of efficiency either in the fermentor or the electrodialysis separator. The mature cells remain viable and are recycled to the fermentor where fermentation continues with addition of carbohydrates and nutrients, and the purified and concentrated lactate from the electrodialyzer can now be used to feed a water splitting electrodialysis system such as the "AQUATECH" system (4) where the lactate salt is converted to lactic acid and alkali. The alkali obtained can be recycled to the fermentor for neutralization, and purified concentrated lactic acid can be used for further processing to make polymers, specialty chemicals or commodity chemical intermediates.

TABLE 2

Comparison of Electrodialysis Runs

|  | Centrifuged and Filtered Broth | |
| --- | --- | --- |
|  | Run I | Run II |
| Lactate Removal, % | 92 | 92 |
| Broth: | | |
| Initial Lactate Conc., g/l | 81 | 75 |
| Final Lactate Conc., g/l | 9 | 9 |
| Concentrate: | | |
| Initial Lactate Conc., g/l | 52 | 72 |
| Final Lactate Conc., g/l | 203 | 196 |
| Length of Run, minutes | 150 | 140 |
| Temperature, °C. (avg.) | 50 | 50 |
| Current Efficiency, % | 92 | 88 |
| Initial Current Density, mamp/cm$^2$ | 67 | 67 |
| Flux, gal/hr-ft$^2$ | 0.17 | 0.18 |
| Average Water Transfer, ml/Fa | 300 | 316 |
| L-amino acids retained, % | | |
| (by enzymatic assay) | 97 | 98 |
| Electricity Requirement, kwhr/lb | 0.08 | 0.08 |

TABLE 3

Comparison of Electrodialysis Runs

|  | Whole Broth | |
| --- | --- | --- |
|  | Run III | Run IV |
| Lactate Removal, % | 82 | 75 |
| Broth: | | |
| Initial Lactate Conc., g/l | 77 | 76 |
| Final Lactate Conc., g/l | 18 | 30 |
| Concentrate: | | |
| Initial Lactate Conc., g/l | 65 | 49 |
| Final Lactate Conc., g/l | 175 | 173 |
| Length of Run, minutes | 140 | 140 |
| Temperature, °C. | 50 | 45 |
| Current Efficiency, % | 90 | 91 |
| Initial Current Density, mamp/cm$^2$ | 56 | 56 |
| Flux, gal/hr-ft$^2$ | 0.17 | 0.15 |
| Average Water Transfer, ml/Fa | 350 | 315 |
| L-amino acids retained, % | | |
| (by enzymatic assay) | 97 | 97 |
| Electricity Requirement, kwhr/lb | 0.08 | 0.11 |

TABLE 4

Protein and Amino Acid Transport

|  | Run II (Centrifuged and Filtered Broth) | | Run III (Whole Broth) | |
| --- | --- | --- | --- | --- |
|  | Feed Broth (filtered) | Product Concentrate | Feed Broth (filtered) | Product Concentrate |
| Volume (l) | 10.6 | 3.75 | 10.6 | 3.25 |
| Total Amino Acids | | | | |
| Concentration (g/l) | 2.93 | 1.27 | 4.58 | 1.47 |
| Weight (g) | 31.06 | 4.76 | 48.55 | 4.78 |
| Rejection (%) | | 84.7% | | 90.2% |
| Free Amino Acids | | | | |
| Concentration (g/l) | 1.15 | 0.44 | 2.41 | 0.77 |
| Weight (g) | 12.2 | 1.65 | 25.55 | 2.5 |
| Rejection (%) | | 86.5% | | 90.2% |

I claim:

1. A process for growing, recovering and purifying lactate from a whole fermentation broth which comprises:
    (a) growing a microorganism having the identifying characteristics of *Lactobacillus acidophilus* IAM 3532 which is capable of producing at least 2 grams of lactate per liter of broth per hour in a fermentor on a carbohydrate containing substrate at a pH of about 5.0 to about 5.7 and a temperature of about 35° to about 45° C. until the broth contains about 75 to about 90 grams of lactate per liter of broth;
    (b) introducing the whole broth containing cells and lactate into an electrodialysis unit having an anode; a cathode; at least one compartment formed by spaced apart anionic-permeable and cationic-permeable membranes; and
    (c) applying electrical current to said membranes to cause lactate anions in said broth in said compartment to permeate through the anionic permeable membrane and concentrate into an aqueous liquid on the other side of said membrane.

2. A process of claim 1 in which the anionic-permeable membrane is a fabric reinforced, microheterogeneous interpolymer membrane.

3. A process of claim 1 in which the cationic-permeable membrane is a fabric reinforced, microheterogeneous interpolymer membrane.

4. A process of claim 1 in which the aqueous liquid is a lactate solution of a monovalent cation.

5. A process of claim 1 in which the electrical current applied to the membranes has an initial current density of about 40 to about 70 mamp/cm$^2$.

6. A process of claim 1 wherein the electrodialysis of the whole broth containing cells establishes purification greater than 85% of soluble proteins and amino acids.

7. A process of claim 1 wherein the electrodialysis of whole broth containing cells is continued for a period of time sufficient to produce a purified concentrate with a lactate concentration of greater than 170 grams/liter.

8. The process of claim 1 which further comprises introducing said aqueous liquid which contains the lactate ions into a water splitting electrodialysis apparatus to convert the lactate to lactic acid.

9. A process of claim 1 in which the whole broth containing

10. A process of claim 8 wherein the whole broth containing cells which is recycled contains viable cells that are capable of further fermenting additional carbohydrates to lactate.

* * * * *

UNITED STATES PATENT AND TRADEMARK OFFICE
CERTIFICATE OF CORRECTION

PATENT NO. : 4,885,247
DATED : December 5, 1989
INVENTOR(S) : Datta

It is certified that error appears in the above-identified patent and that said Letters Patent is hereby corrected as shown below:

Column 10, line 63    After "containing" insert --cells from which lactate has been removed is recycled to the fermentor.--

Signed and Sealed this

Twenty-fifth Day of January, 1994

Attest:

BRUCE LEHMAN

Attesting Officer    Commissioner of Patents and Trademarks